United States Patent [19]

Lyford, IV

[11] Patent Number: 5,532,405

[45] Date of Patent: Jul. 2, 1996

[54] PREPARATION OF PLASTICIZER OR POLYOL ESTERS BY THE STAGED ADDITION OF THE LOWER BOILING POINT REACTANT

[75] Inventor: John Lyford, IV, Baton Rouge, La.

[73] Assignee: Exxon Chemical Patents Inc., Wilmington, Del.

[21] Appl. No.: 235,821

[22] Filed: Apr. 29, 1994

[51] Int. Cl.[6] ............................................. C07C 67/08
[52] U.S. Cl. ........................... 560/99; 560/98; 560/103; 560/204
[58] Field of Search .................. 560/98, 99, 103, 560/204

[56] References Cited

U.S. PATENT DOCUMENTS

| | | | |
|---|---|---|---|
| 2,411,136 | 11/1946 | Luce | 260/485 |
| 2,813,891 | 11/1957 | Billing | 260/475 |
| 3,681,434 | 8/1972 | Neely | 260/475 B |
| 4,077,945 | 3/1978 | Heinze et al. | 260/75 M |
| 4,241,216 | 12/1980 | Bergman et al. | 560/99 |
| 4,859,792 | 8/1989 | Powanda et al. | 560/204 |
| 4,868,329 | 9/1989 | Powanda et al. | 560/205 |
| 5,324,853 | 6/1994 | Jones et al. | 560/98 |

FOREIGN PATENT DOCUMENTS

| | | |
|---|---|---|
| 625203 | 4/1947 | European Pat. Off. . |
| 0331844 | 9/1989 | European Pat. Off. . |
| 0434390 | 6/1991 | European Pat. Off. . |
| SU1022-964-A | 11/1980 | Greece ............ C07C 69/80 |
| 1290361 | 9/1972 | United Kingdom . |

*Primary Examiner*—José G. Dees
*Assistant Examiner*—Rosalynd A. Williams
*Attorney, Agent, or Firm*—Richard D. Jordan

[57] ABSTRACT

A process for the esterification of acids or anhydrides with alcohols or a polyhydroxy compound wherein the lower boiling point reactant is added to the reaction vessel in stages such that it is present in an amount of at least about 5% of the stoichiometric requirements of the total lower boiling point reactant required to react with the limiting reagent, and wherein the concentration of the lower boiling point reactant is monitored so that additional reactant having the lower boiling point can be subsequently added in stages to the reaction mixture in order to maintain a certain predetermined concentration of the lower boiling point reactant.

21 Claims, 2 Drawing Sheets

PREPARATION OF PLASTICIZER OR POLYOL ESTERS BY THE STAGED ADDITION OF THE LOWER BOILING POINT REACTANT

The present invention is directed primarily to a process for preparing plasticizer esters for polyvinylchloride (PVC) such as phthalates, adipates and trimellitates in the presence of a titanium, zirconium or tin-based catalyst or acid catalyst. It is also useful for preparing polyol esters in the presence of excess acid and, optionally, a catalyst. The rate of the esterification reaction is increased due to rapid increase in the temperature of the reaction mixture which is brought on by the staged addition of the lower boiling point reactant.

BACKGROUND OF THE INVENTION

The reaction conditions under which esterification is effected can be varied considerably. The reaction proceeds very slowly at room temperature, but quite rapidly at elevated temperatures. About 99% of the limiting reagent, e.g., acids, anhydrides or polyols, is converted to an ester within a few hours. Limiting reagents are typically reagents which are not present in stoichiometric excess, e.g., limiting reagents used to make plasticizers include diacids and phthalic anhydride and those used to make polyol esters are polyols.

In the production of esters by the reaction of an acid or anhydride with at least one alcohol or polyol, water is a by-product of the reaction. Since the reaction is an equilibrium reaction, it is forced to completion by the removal of the water by-product, typically through distillation of the water from the reaction mixture during the esterification process. Frequently, an entrainer is used to aid in the distillation of the water from the reaction mixture. Inert materials such as benzene, toluene, or xylene may be used as the entrainer. In addition, the reactant having the lower boiling point has also been employed as the entrainer. In this latter case, the reactant used as the entrainer is charged into the reaction mixture in excess over the stoichiometric quantities required for the reaction.

The conventional procedure is to charge all of the reactants into the reactor at the beginning of the reaction cycle. The reaction mixture is then heated and reaction begins. The temperature of the reaction mixture rises until the boiling point of the reaction mixture is achieved, at which point the entrainer and water by-product boil out of the reaction mixture. Typically, the overhead vapors are condensed, the water separated from the entrainer, and the entrainer recycled to the reactor vessel. The reaction temperature, and therefore the rate of reaction, are thus determined by the boiling point of the reaction mixture.

When the reactant with the lower boiling point is also used as the entrainer, its concentration is gradually reduced as the reaction proceeds. Thus the reaction temperature, and therefore the rate constant for the reaction, increases as the reaction proceeds.

The present invention is not only economically desirable, but it also substantially increases the overall rate at which the reactants are converted to esters. In general, for a given conversion the lower the water content, the faster the rate of reaction.

The present invention provides a novel method for increasing the rate of esterification reaction, wherein only a portion of the lower boiling point reactant is added to the reactor at the outset, followed by the staged or subsequent addition of the remaining portion of the lower boiling point reactant throughout the remainder of the esterification reaction. Since the concentration of the lower boiling point reactant in the reaction mixture is less in the present invention than in the conventional esterification process wherein all of the lower boiling point reactant is added to the reaction mixture at the outset, the temperature of the reaction mixture will be higher over time than the temperature in the conventional case. Consequently, the reaction temperature, and therefore the rate of reaction, will be higher during staged addition of the lower boiling point reactant than during conventional processing. The higher rate of reaction translates into a shorter reaction time for the staged addition process than for the conventional batch process. As the reaction proceeds and the concentration of the lower boiling point reactant is depleted, additional amounts of this reactant are added to the reaction mixture in stages to ensure that it is present in sufficient quantities to satisfy the reaction requirements. At the completion of the reaction, the same total amount of the lower boiling point reactant has been used in the staged addition process as in the conventional batch process wherein all of the reactants are charged to the reactor at the outset.

The present invention also provides many additional advantages which shall become apparent as described below.

SUMMARY OF THE INVENTION

A process for the esterification of acids with at least one alcohol which comprises the following steps: (a) adding an acid and at least one alcohol to a reaction vessel to form a reaction mixture, the alcohol being added in an amount of at least about 5% of the stoichiometric requirements of the total alcohol required to react with the acid; (b) heating the reaction mixture to a temperature at about or above the boiling point of the alcohol and maintaining a pressure sufficient to obtain boiling of the reaction mixture, thereby converting the acid and the alcohol to an ester and removing water and a portion of the alcohol from the reaction vessel; (c) monitoring the concentration of the alcohol in step (b); and (d) adding additional alcohol to the reaction mixture to maintain a certain predetermined concentration of alcohol.

The monitoring in step (c) is preferably conducted by titrating the reaction mixture to determine its acidity concentration, measuring the water evolved from the reaction mixture, computer modeling of the reaction rate, or any other means capable of monitoring the concentration of the lower boiling point reactant within the reaction mixture.

The process further comprises the addition of a catalyst to the reaction vessel such that the acid and alcohol are catalytically converted to the ester.

Preferably, a portion of the alcohol and water by-product form an azeotrope which is removed from the reaction vessel via distillation. The distilled alcohol and water are thereafter separated such that the alcohol can be recycled back to the reaction vessel.

This staged esterification of the lower boiling point reactant is also applicable to the formation of polyol esters, i.e., the acids are added to a polyhydroxy compound in stages in order to insure that the acid concentration within the reaction mixture is maintained at a level of at least 5% of the stoichiometric requirements of the total acids required to react with the polyhydroxy compounds.

It is also useful in forming plasticizer esters from an anhydride and at least one alcohol, wherein the anhydride and alcohol(s) are added to the reaction vessel in stoichiometric equivalents to form an intermediate reaction product which reacts with additional alcohol to form the reaction mixture. During the formation of the intermediate reaction product the stoichiometric equivalents are the amount of alcohol which is needed to form the monoester, i.e., one alcohol to one anhydride. Additional alcohol is present at the outset in an amount of at least about 5% of the stoichiometric requirements of the total alcohol required to react with the anhydride. The stoichiometric requirements for forming the diester is approximately two alcohols to one anhydride. The reaction mixture is thereafter heated, monitored for alcohol concentration, and treated with additional alcohol as needed to maintain a predetermined alcohol concentration.

DESCRIPTION OF THE PREFERRED EMBODIMENTS

Figure 1:
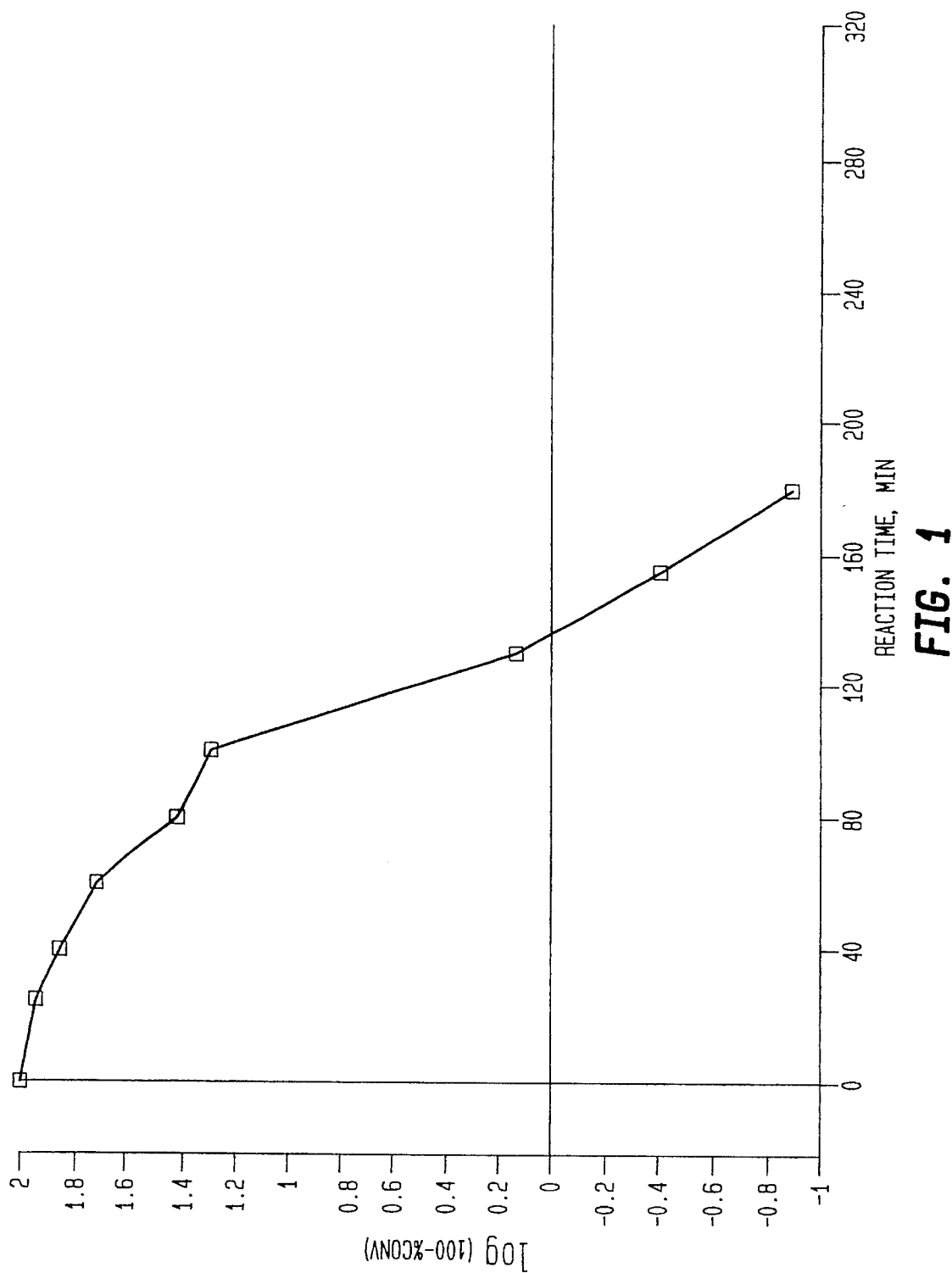
FIG. 1 is a graph plotting log(100-% conversion) versus reaction time for a conventional esterification process wherein all the alcohol is added at the outset of the reaction.

Reaction temperatures in esterification reactions are frequently determined by the boiling point of the reaction mixture. Staging the addition to the reaction mixture of the reactant having the lower boiling point results in reaction mixtures with higher boiling points in the early phases of the reaction. These higher boiling points translate into higher reaction temperatures, resulting in shorter reaction times in achieving a given conversion. This invention is particularly applicable to the production of phthalates, adipates, trimellitates, and polyols, as well as the production of other esters in which one of the reactants is volatile under reaction conditions.

The preferred process for the esterification of acids with at least one alcohol in accordance with the present invention involves the addition of an acid and at least one alcohol into a reaction vessel to form a reaction mixture. The reactant with the highest boiling point is added to the reaction vessel in its entirety at the beginning of the reaction. Thereafter, the reactant with the lower boiling point is added in stages such that it has an amount of at least about 5% of the stoichiometric requirements of the total lower boiling point reactant required to react with the higher boiling point reactant. For example, if the alcohol reactant has a lower boiling point than the acid, then it is typically added to the reaction vessel a portion at a time (i.e., in stages) such that it is always present within the reaction vessel in an amount of at least about 5% of the stoichiometric requirements of the total alcohol required to react with the acid. More preferably, the alcohol is present in an amount of from about 5% to 60%, most preferably from about 10% to 20% of the stoichiometric requirements of the total alcohol necessary to react with the acid.

Plasticizer esters may also be formed by reacting an anhydride with at least one alcohol. The anhydride and alcohol are added to the reaction vessel in stoichiometric equivalents to form an intermediate reaction product. Simultaneously, additional alcohol is added to the reaction vessel in an amount of at least about 5% of the stoichiometric requirements of the total alcohol required to react with the anhydride, thereby forming a reaction mixture.

This process can also be used to convert polyols and acids to polyol esters. The polyol ester process typically comprises the steps of esterification of the starting acid with a polyol and, optionally, a catalyst. In this instance the acid, or mixture of acids, is added to the reaction mixture in stages such that it is present in an amount of at least about 5% of the stoichiometric requirements of the total acid required to react with the polyol. The reaction mixture is continuously monitored such that a predetermined level of acid is maintained by the staged addition of additional acids when needed.

The esterification process may also include one or more of the following steps: removal of excess acid by nitrogen or steam stripping; addition of adsorbents such as alumina, silica gel, activated carbon, clay and/or filter aid to the reaction mixture following esterification before further treatment, but in certain cases adsorbent treatment may occur later in the process following steam stripping and in still other cases the adsorbent step may be eliminated from the process altogether; addition of water and base to simultaneously neutralize the residual organic acids and hydrolyze the catalyst (if present); filtration of solids from the ester mixture containing the bulk of the excess acid by steam or nitrogen stripping under vacuum and recycling of the acid to the reaction vessel; and removing solids from the stripped ester in a final filtration.

The staged addition of the reactant having the lower boiling point allows for a more rapid heating of the reaction mixture due to the change in boiling point of the reaction mixture which in turn produces a higher rate of reaction. The reason that the reactant having the lower boiling point is added in stoichiometric excess over the reactant having the higher boiling point is to ensure that there is sufficient amount of the lower boiling point reactant contained within the reaction vessel at any one time to ensure sufficient esterification while simultaneously acting as an entrainer which is capable of forming an azeotrope with the water by-product for distilling the water out of the reactor. The refluxed entrainer and water is then separated such that the distilled reactant can be recycled back to the reaction mixture. It is also important to maintain a reaction temperature at or above the boiling point of the reactant having the lower boiling point in order to promote the formation of an azeotrope with the water by-product.

The pressure of the reaction vessel should also be maintained at a level sufficient to reflux the alcohol or acid (entrainer) and the water while forming an ester from the reactants.

ESTERIFICATION CATALYST

The esterification process is preferably conducted in the presence of a catalyst. Typical esterification catalysts are titanium, zirconium and tin catalysts such as titanium, zirconium and tin alcoholates, carboxylates and chelates. See U.S. Pat. No. 3,056,818 (Werber) which issued on Oct. 2, 1962, and which is incorporated herein by reference.

Typical titanium alcoholates which can be used as catalysts include tetramethyl titanates, tetraethyl titanates, tetrapropyl titanates, tetra-isopropyl titanates, tetrabutyl titanates, tetrapentyl titanates, tetrahexyl titanates, tetra-octyl titanates, tetranonyl titanates, tetradodecyl titanates, tetrahexadecyl titanates, tetra-octadecyl titanates, tetradecyl titanates, tetraheptyl titanates and tetraphenyl titanates. The alkyoxy groups on the titanium atom can all be the same or they can be different. The zirconium counterparts of the above alcoholates can be substituted in whole or in part as catalysts.

The titanium carboxylates which serve as esterification catalysts are polymeric materials having at least one acyl group for each titanium atom. Typical titanium acylates which can be employed as catalysts include acylates from 2 to 18 carbon atoms, such as hydroxy titanium acetate, hydroxyl titanium butyrate, hydroxy titanium pentanoate, hydroxy titanium hexanoate, hydroxy titanium octanoate, hydroxy titanium decanoate, hydroxy titanium dodecanoate, hydroxy titanium tetradecanoate, hydroxy titanium hexadecanoate, hydroxy titanium octadecanoate, hydroxy titanium oleate, hydroxy titanium soya acylate, hydroxy titanium linseed acylate, hydroxy titanium castor acylate, hydroxy titanium tall oil acylate, hydroxy titanium coconut acylate, methoxy titanium acetate, ethoxy titanium butyrate, isopropoxy titanium pentanoate, butoxy titanium hexanoate, isopropoxy titanium octanoate, isopropoxy titanium decanoate, isopropyl titanium dodecanoate, isopropoxy titanium tetradecanoate, isopropoxy hexadecanoate, isopropoxy octadecanoate, isopropoxy titanium oleate, isopropoxy titanium soya acylate, isopropoxy linseed acylate, isopropoxy coconut acylate. The alkoxy group of the acylate can vary from 1 to 20 carbon atoms. The corresponding zirconium carboxylates can be used as catalysts.

Titanium chelates are formed by reacting a titanium compound with a polyfunctional molecule including polyols such as glycols or glycerine and amino alcohols, amino acids, hydroxy acids and polycarboxylic acids. Typical chelated esters which serve as catalysts include tetra-ethylene glycol titanate, tetrapropylene glycol titanate, tetrabutylene glycol titanate, tetra-octylene glycol titanate and tetrapolyethylene glycol titanate, dibutoxy di-(ethylene glycol) titanate, di-isopropoxy di-(octylene glycol) titanates, dimethoxy di-(octylene glycol) titanates, diethyoxy di-(octylene glycol) titanates, tetratriethanol amine titanate, tetratriethanol amine-N-oleate titanate, triethanol amine-N-stearate titanate, triethanol amine-N-linseed acid salt titanate, dibutoxy titanate, dipropoxy titanate, dimethoxy titanate, diethoxy titanate, other dialkoxy dipropoxy, dimethoxy, diethoxy titanates, and other dialkoxy di-(amino alcohol) titanates. The corresponding zirconium chelates are also useful as catalysts.

Selected acid catalysts may also be used in this esterification process. Some examples of acid catalysts are: sulfuric acid, benzene sulfonic acid, p-toluene sulfonic acid, naphthalene sulfonic acid, aluminum sulfate, aluminum powder, normal decylbenzene sulfonic acid, normal dodecylbenzene sulfonic acid, normal nonylbenzene sulfonic acid, normal octylbenzene sulfonic acid, normal heptylbenzene sulfonic acid, normal hexylbenzene sulfonic acid, normal tridecylbenzene sulfonic acid, normal tetradecylbenzene sulfonic acid, normal dodecane sulfonic acid, normal tridecane sulfonic acid, normal tetradecane sulfonic acid, normal pentadecane sulfonic acid, normal hexadecane sulfonic acid, normal heptadecane sulfonic acid, normal octadecane sulfonic acid, normal nonadecane sulfonic acid, normal eicosane sulfonic acid, 3-methyldodecane sulfonic acid, 3-methyl-5-ethyldecane sulfonic acid, 3-methyldecylbenzene sulfonic acid, 4-ethyloctylbenzene sulfonic acid, phosphoric acid, aromatic phosphonic acids (e.g., organic disulfonic acids, 1,2-ethanedisulfonic acid, 1,3-propanedisulfonic acid, m-benzene disulfonic acid, 2,5-, 2,6-, or 2,7-naphthalene disulfonic acids or mixtures of these isomers, and 3,5-o-xylenedisulfonic acid), acidic formalite resins prepared by reacting an aromatic hydrocarbon, an aldehyde, and sulfuric acid, methane disulfonic acid, methane trisulfonic acid, hydrochloric acid, perfluorinated resin sulfonic acid, acidic ion exchange resins, chlorosulfonic acid, thionyl chloride, boron trifluoride, dihydroxy fluoride, dihydroxy fluoboric acid, and silicon tetrafluoride.

ACIDS

Carboxylic acids which undergo esterification (i.e., mono or poly-basic acids, preferably dibasic or tribasic acids) can be aliphatic, cyclo-aliphatic or aromatic, they can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, isovaleric, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, citric, acrylic, alpha-chloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$ and $C_{10}$ (e.g., 3,5,5-trimethylhexanoic) and branched $C_{17}$, $C_{19}$, $C_{21}$, etc., acids.

Among the alicyclic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,4-cyclohexane dicarboxylic, cyclohexane-1,2,3,4,5,6-hexacarboxylic, cyclopentene-2-carboxylic, 1-cyclohexene-1-carboxylic, hydrocapric, cyclohexadiene- 1,2-dicarboxylic, and 1,3-cyclohexadiene-1,4-dicarboxylic.

The aromatic acids include benzoic, o-, m- and p-chloro and bromo benzoic, o-, m- and p-hydroxy benzoic, o-, m- and p-nitrobenzoic, o-, m- and p-methoxy benzoic, alpha-napthoic, beta-naphthoic, o-, m- and p-methyl benzoic, o-, m- and p-ethyl benzoic, p-phenyl benzoic, phthalic, isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic.

When polyols are used to form an ester the following acids are preferred: neopentanoic acid, neoheptanoic, neooctanoic acid, neononanoic acid, neodecanoic acid, 2-ethyl hexanoic acid, oxo-heptanoic acid (i.e., a mix of isomers derived from oxonation/oxidation of hexenes), oxo-decanoic acid (i.e., a mix of isomers derived from oxonation/oxidation of mixed nonenes), oxo-octanoic acid (i.e., a mix of isomers derived from oxonation/oxidation of mixed heptenes), 3,5,5-trimethylhexanoic acid, linear $C_5$–$C_{18}$ alkanoic acids, and blends thereof.

ANHYDRIDES

Anhydrides of mono- and poly-basic acids can be used in place of the acids, especially when plasticizer esters are being formed. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride is pyromellitic dianhydride.

ALCOHOLS

Among the alcohols which can be reacted with acids and anhydrides are, by way of example, most primary and secondary $C_1$–$C_{30}$ monohydric or polyhydric, substituted or unsubstituted alkanols and alkenols, such as, methanol, ethanol, chloroethanol, cyanoethanol, ethoxyethanol, phenylethanol, n-propanol, 2-chloropropanol-1, 3-bromo-propanol-1, 2,2-dichloropropanol-1, isopropanol, propanol-2, 2-nitrobutanol-1, 2 -nitrobutanol-1, 2-methylpentanol-1, 2-methyl pentanol- 3, the primary and secondary octanols, n-dodecanol, 6-dodecanol, lauryl, myristyl, stearyl, 2-propenol-1, 2 -butenol-1, 3-pentenol-1, ethylene glycol, trimethylene glycol, tetramethylene glycol, pentamethylene glycol, glycerol, 1,4-butanediol, decane-1,10-diol, pentadecane-1,15-diol, pentacosane-1,25-diol, 2,4 -hexadiene-1,6-diol, 2,4-octadiene-1,8-diol, and aromatic alcohols such as benzyl alcohol, o-, m- and p-methoxy alcohol, o-, m- and p-nitrobenzyl alcohol, o-, m- and p-methyl benzyl alcohol, phenyl ethyl alcohol, triphenyl ethyl alcohol, o-, m- and p-benzyl benzyl alcohol, alpha-naphthyl-ethyl alcohol, beta-naphthyl ethyl alcohol, naphthylene-1,2-diethyl alcohol, phenylene-1,3,5-triethyl alcohol, and phenylene-1,4-dioctyl alcohols. This includes higher Guerbet alcohols which are beta carbon branched dimer alcohols having ten to twenty-six carbon atoms.

Polyol (i.e., polyhydroxy compounds) are represented by the general formula:

wherein R is an alkyl, alkenyl or aralkyl hydrocarbyl group and n is at least 2, and can be used in place of the mono alcohols when polyol esters are desired. The hydrocarbyl group may contain from about 2 to 20 or more carbon atoms, and the hydrocarbyl group may also contain substituents such as chlorine, nitrogen and/or oxygen atoms. The polyhydroxy compounds generally will contain from about 2 to 10 hydroxy groups and more preferably from about 2 to 6 hydroxy groups. The polyhydroxy compound may contain one or more oxyalkylene groups and, thus, the polyhydroxy compounds include compounds such as polyetherpolyols. The number of carbon atoms and number of hydroxy groups contained in the polyhydroxy compound used to form the carboxylic esters may vary over a wide range.

The following alcohols are particularly useful as polyols: neopentyl glycol, 2,2-dimethylol butane, trimethylol ethane, trimethylol propane, trimethylol butane, mono and technical grade (i.e., 88% mono, 10% di and 1–2% tri) pentaerythritol, dipentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol).

The method according to the present invention is capable of forming plasticizer esters, such as, phthalates, adipates and trimellitates, from $C_4$–$C_{15}$ alcohols, preferably $C_6$–$C_{13}$ oxo-alcohols. Because of the increase in the rate of reaction, in accordance with this invention, the process is particularly useful in esterifications catalyzed by titanium, zirconium, or tin containing catalysts.

This method, with or without the above mentioned titanium, zirconium, or tin-based catalysts, is also useful in forming polyol esters, such as, neopolyol esters, from polyols and excess fatty acids. The polyol or polyol mixture is preferably technical grade pentaerythritol (PE), trimethyolpropane (TMP), and neopentylglycol each which can be admixed with monopentaerythritol and/or trimethylol propane or other neopolyols. The preferred acid component is typically a mixture of straight chain acids having five to ten carbon atoms, or a branched chain acid having from five to eighteen carbon atoms, preferably five to nine carbon atoms, namely 2-methylhexanoic, 2-ethylpentanoic, 3,5,5-trimethylhexanoic acids or mixtures thereof. Generally, the acids are monocarboxylic acids. Suitable straight chain acids include, but are not limited to, valeric acid ($C_5$), enanthic acid ($C_7$), caprylic acid ($C_8$), pelargonic acid ($C_9$), and capric acid ($C_{10}$).

The branched chain acid may be iso-$C_5$, iso-$C_7$, iso-$C_8$ or iso-$C_9$. Preferably, the branched chain acid used is the iso-$C_7$ acid. Another preferred branched acid is 3,5,5-trimethylhexanoic acid derived from the oxonation/oxidation of diisobutylene. Still another preferred branched acid is oxo-octanoic acid derived from the oxonation/oxidation of mixed heptenes.

In the reaction used to form polyol esters, the acid mixture is present in an excess of about 10 to 50 mole percent or more for the amount of polyol used. The excess acid is used to force the reaction to completion. The composition of the feed acid is adjusted so as to provide the desired composition of product ester. After the reaction is complete, the excess acid is removed by stripping and additional finishing.

According to one preferred embodiment of the present invention, phthalic anhydride and hexyl alcohol are initially added to the reaction vessel in a molar ratio of between about 1:1.05 to 1:1.4. Thereafter, an additional 1 mole of hexyl alcohol is added to the reaction mixture as needed to maintain a molar excess of alcohol within the reaction mixture. The phthalic anhydride and phthalic ester have a molar ratio of approximately 1:1.

EXAMPLE 1

A pair of esterification reactions were run under the same conditions to compare their rates of reaction. The first reaction followed the conventional batch process technique by adding all of the lower boiling point reactant (i.e., hexyl alcohol) at the beginning of the reaction. The second reaction involved the staged addition of hexyl alcohol to insure that the hexyl alcohol concentration in the reaction mixture was maintained at an amount of about 20% of the stoichiometric requirements of the total hexyl alcohol required to react with the phthalic anhydride.

In the first reaction, 363 grams of phthalic anhydride were added to a reaction vessel together with 600 grams of hexyl alcohol in the presence of 0.98 grams of a tetraisopropyl titanate catalyst. The initial temperature of the reaction mixture was 22° C. The reaction mixture was then heated for 25 minutes to a temperature of 170° C. at which temperature the reaction mixture began to reflux. After 155 minutes the reaction mixture reached a temperature of 220° C. 99% of the phthalic anhydride was converted to a phthalic ester within 137 minutes. FIG. 1 is a graphic representation of the results of the first reaction in this example.

Figure 2:
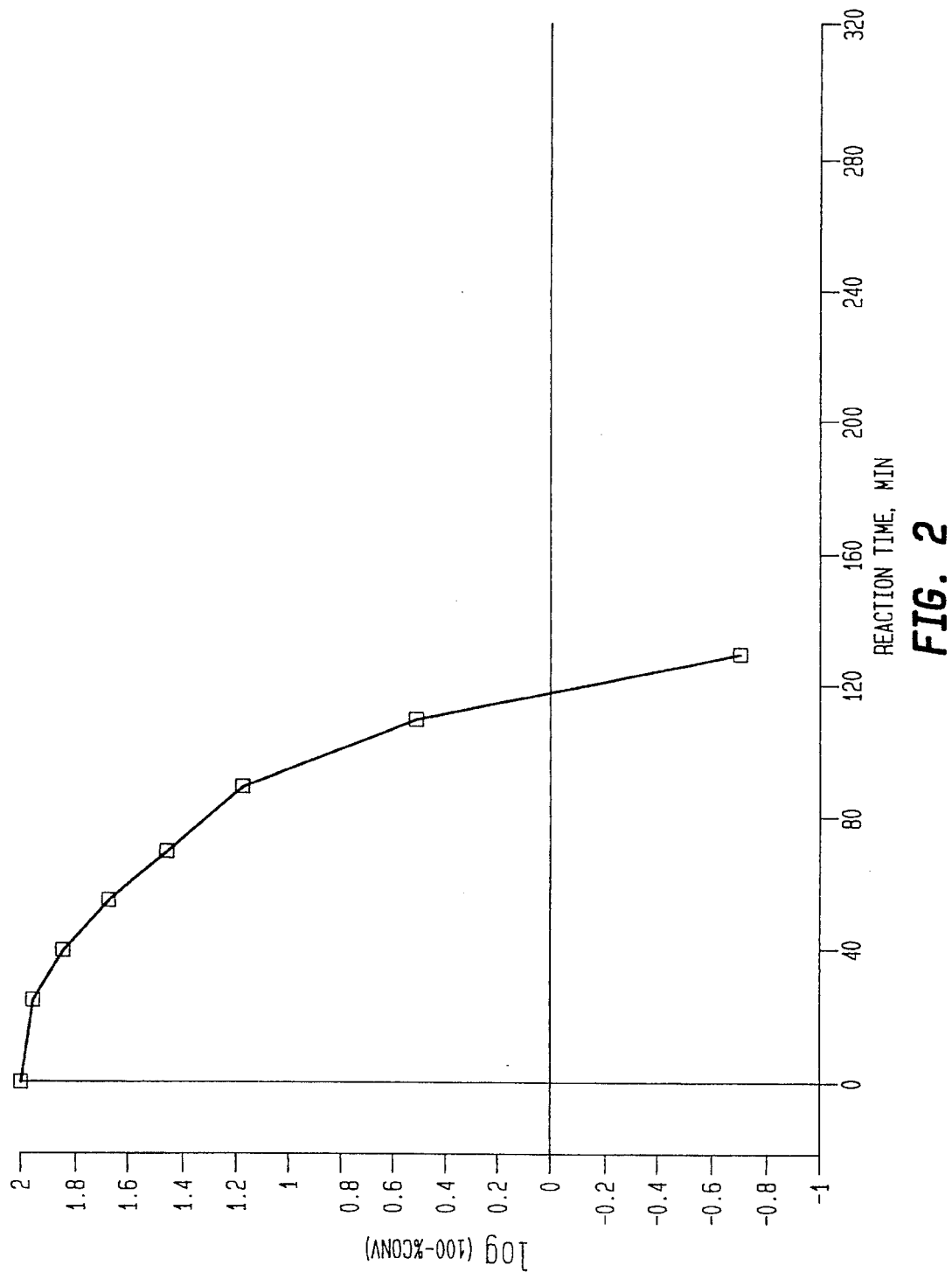
FIG. 2 is a graph plotting log(100-% conversion) versus reaction time for an esterification process according to the present invention wherein the addition of the alcohol is staged throughout the entire esterification reaction in order to maintain an alcohol concentration in the reaction vessel in an amount of about 20% of the stoichiometric requirements of the total alcohol required to react with the anhydride.

In the second reaction, 363 grams of phthalic anhydride were added to a reaction vessel together with 350 grams of hexyl alcohol in the presence of 0.98 grams of a tetraisopropyl titanate catalyst. The initial temperature of the reaction mixture was 18° C. The reaction mixture was then heated for 25 minutes to a temperature of 188° C. at which temperature the reaction mixture began to reflux. The remaining 250 grams of hexyl alcohol was added in stages throughout the esterification process so as to maintain a relatively constant quantity of unreacted alcohol in the reaction mixture. The reaction rate itself is constantly changing overtime. After 70 minutes the reaction mixture reached a temperature of 220° C. 99% of the phthalic anhydride was converted to a phthalic ester within 125 minutes. FIG. 2 is a graphic representation of the results of the second reaction in this second example.

Comparison of the two reactions demonstrates that higher temperatures and, thus, faster ester conversion was attained via staged addition of the hexyl alcohol, which has a lower boiling point than the phthalic anhydride. That is, when all the hexyl alcohol was added to the reaction vessel at the outset, it took 155 minutes to reach a temperature of 220° C. and 137 minutes to reach 99% conversion. The staged addition of the hexyl alcohol caused the reaction mixture to reach 220° C. in about 70 minutes, more than twice as fast as the first reaction. Moreover, the second reaction having staged alcohol addition also reached 99% conversion of phthalic anhydride to phthalic ester in 125 minutes, approximately 10% faster than the conventional first reaction.

EXAMPLE 2

The conventional batch process wherein all of the reactants were added to the reaction vessel at the outset of the reaction was examined to demonstrate its reaction time for comparable ester conversion rates verses the reaction time obtained when lower boiling point reactants are added in stages. In this example, 348 grams of technical grade pentaerythritol was charged into an esterification reactor together with all of the $C_5$ acid (855 grams) and $C_9$ acid (570 grams) used during the reaction. Theoretical water was present in an amount of 180 grams. The results are set forth below in Table 1.

TABLE 1

| Time (min) | Temp. (°C.) | Pressure (MM HG) | H2O (ml) | Conv. (%) | (100% Conv.) | Log (100% Conv.) |
|---|---|---|---|---|---|---|
| 0 | 17.8 | 50 | 0 | 0.00 | 0 | 0 |
| 30 | 80 | 50 | 0 | 0.00 | 100 | 2 |
| 40 | 108.9 | 50 | 0 | 0.00 | 100 | 2 |
| 70 | 160 | 50 | 10 | 5.56 | 94.44 | 1.97 |
| 78 | 161.1 | 50 | 20 | 11.12 | 88.88 | 1.95 |
| 83 | 163.9 | 50 | 30 | 16.68 | 83.32 | 1.92 |
| 89 | 166.1 | 50 | 40 | 22.23 | 77.76 | 1.89 |
| 96 | 168.3 | 50 | 50 | 27.79 | 72.21 | 1.86 |
| 103 | 170.5 | 50 | 60 | 33.35 | 66.64 | 1.82 |
| 110 | 173.5 | 50 | 70 | 38.91 | 61.09 | 1.79 |
| 118 | 175.5 | 50 | 80 | 44.47 | 55.53 | 1.74 |
| 127 | 178.3 | 50 | 90 | 50.03 | 49.97 | 1.70 |
| 136 | 182.2 | 50 | 100 | 54.49 | 44.41 | 1.65 |
| 148 | 185.5 | 50 | 110 | 61.15 | 38.85 | 1.59 |
| 159 | 190.5 | 50 | 120 | 66.70 | 33.29 | 1.52 |
| 173 | 193.9 | 50 | 130 | 72.26 | 27.74 | 1.44 |
| 184 | 198.9 | 50 | 135 | 75.04 | 24.96 | 1.40 |
| 192 | 200.5 | 50 | 140 | 77.82 | 22.18 | 1.35 |
| 212 | 206.1 | 50 | 150 | 83.38 | 16.62 | 1.22 |
| 239 | 215.5 | 50 | 160 | 88.94 | 11.06 | 1.04 |
| 242 | 216.1 | 50 | 161 | 89.49 | 10.51 | 1.02 |
| 244 | 218.3 | 50 | 162 | 90.05 | 9.95 | 1.00 |

TABLE 1-continued

| Time (min) | Temp. (°C.) | Pressure (MM HG) | H2O (ml) | Conv. (%) | (100% Conv.) | Log (100% Conv.) |
|---|---|---|---|---|---|---|
| 250 | 215 | 50 | 163 | 90.61 | 9.39 | 0.97 |
| 261 | 215 | 50 | 166 | 92.27 | 7.73 | 0.89 |
| 274 | 215.5 | 50 | 168.6 | 93.72 | 6.28 | 0.80 |
| 281 | 215.5 | 50 | 170 | 94.50 | 5.50 | 0.74 |
| 290 | 215.5 | 50 | 170.8 | 94.94 | 5.06 | 0.70 |

EXAMPLE 3

In this example, 348 grams of technical grade pentaerythritol was initially charged into an esterification reactor at the beginning of the reaction together with 428 grams of a $C_5$ acid (valeric acid) and 285 grams of a $C_9$ acid (branched chain iso-$C_9$). Theoretical water was present in an amount of 180 grams. Thereafter, the remaining 427 grams of the $C_5$ acid and 285 grams of the $C_9$ acid were added in stages during the esterification reaction. The results are set forth below in Table 2.

TABLE 2

| Time (min) | Temp. (°C.) | Pressure (MM HG) | H2O (ml) | Conv. (%) | Acid (ml) | (100% Conv.) | Log (100% Conv.) |
|---|---|---|---|---|---|---|---|
| 0 | 18.3 | 50 | 0 | 0.00 | | 100 | 2 |
| 22 | 79.4 | 50 | 0 | 0.00 | | 100 | 2 |
| 27 | 106.1 | 50 | 0 | 0.00 | | 100 | 2 |
| 32 | 122.8 | 50 | 0 | 0.00 | | 100 | 2 |
| 35 | 136.7 | 50 | 0.8 | 0.44 | | 99.55 | 2 |
| 38 | 146.1 | 50 | 1 | 0.56 | | 99.44 | 2 |
| 41 | 152.8 | 50 | 2 | 1.11 | | 98.89 | 1.99 |
| 45 | 158.3 | 50 | 5 | 2.78 | | 97.22 | 1.99 |
| 48 | 162.8 | 50 | 6.8 | 3.78 | | 96.22 | 1.98 |
| 50 | 166.7 | 50 | 10 | 5.56 | | 94.44 | 1.97 |
| 56 | 174.4 | 50 | 16.5 | 9.17 | | 90.82 | 1.96 |
| 58 | 175.0 | 50 | 20 | 11.12 | | 88.88 | 1.95 |
| 61 | 176.7 | 50 | 25 | 13.90 | | 86.10 | 1.93 |
| 64 | 176.7 | 50 | 30 | 16.68 | | 83.32 | 1.92 |
| 68 | 180.0 | 50 | 35 | 19.46 | | 80.54 | 1.91 |
| 71 | 181.1 | 50 | 40 | 22.23 | 0 | 77.76 | 1.89 |
| 74 | 182.2 | 50 | 44.2 | 24.57 | 40 | 75.43 | 1.877 |
| 77 | 181.1 | 50 | 46.2 | 25.68 | 70 | 74.32 | 1.87 |
| 80 | 181.1 | 50 | 50 | 27.79 | 100 | 72.21 | 1.86 |
| 85 | 183.3 | 50 | 55 | 30.57 | 145 | 69.43 | 1.84 |
| 89 | 183.3 | 50 | 60 | 33.35 | | 66.65 | 1.82 |
| 94 | 185.0 | 50 | 65 | 36.13 | 225 | 63.87 | 1.80 |
| 98 | 185.0 | 50 | 70 | 38.91 | | 61.09 | 1.79 |
| 101 | 173.3 | 50 | 72 | 40.02 | 500 | 59.98 | 1.78 |
| 104 | 174.4 | 50 | 74 | 41.13 | | 58.87 | 1.77 |
| 105 | 176.1 | 50 | 75 | 41.69 | 510 | 58.31 | 1.77 |
| 110 | 179.4 | 50 | 80 | 44.47 | 540 | 55.53 | 1.74 |
| 115 | 180.5 | 50 | 85 | 47.25 | 605 | 52.75 | 1.72 |
| 120 | 180.5 | 50 | 90 | 50.03 | 655 | 49.97 | 1.70 |

EXAMPLE 4

In this example, 348 grams of technical grade pentaerythritol was initially charged into an esterification reactor at the beginning of the reaction together with 570 grams of a $C_5$ acid (valeric acid) and 380 grams of a $C_9$ acid (branched chain iso-$C_9$). Theoretical water was present in an amount of 180 grams. Thereafter, the remaining 285 grams of the $C_5$ acid and 190 grams of the $C_9$ acid was added in stages during the esterification reaction. The results are set forth below in Table 3.

TABLE 3

| Time (min) | Temp. (°C.) | Pressure (MM HG) | H2O (ml) | Conv. (%) | Acid (ml) | (100% Conv.) | Log (100% Conv.) |
|---|---|---|---|---|---|---|---|
| 0 | 18.3 | 50 | 0 | 0.00 | | 100 | 2 |
| 22 | 79.4 | 50 | 0 | 0.00 | | 100 | 2 |
| 29 | 110 | 50 | 0 | 0.00 | | 100 | 2 |
| 32 | 117.8 | 50 | 0 | 0.00 | | 100 | 2 |
| 35 | 127.2 | 50 | 0.3 | 0.17 | | 99.83 | 2 |
| 38 | 136.7 | 50 | 0.8 | 0.44 | | 99.55 | 2 |
| 41 | 144.4 | 50 | 1.5 | 0.83 | | 99.17 | 2 |
| 45 | 152.8 | 50 | 2.5 | 1.39 | | 98.61 | 2 |
| 48 | 157.8 | 50 | 4.5 | 2.50 | | 97.50 | 1.99 |
| 51 | 163.3 | 50 | 7.5 | 4.17 | | 95.83 | 1.98 |
| 53 | 166.7 | 50 | 10 | 5.56 | | 94.44 | 1.97 |
| 57 | 170.5 | 50 | 15 | 8.34 | | 91.66 | 1.96 |
| 59 | 169.4 | 50 | 19.2 | 10.67 | 20 | 89.33 | 1.95 |
| 60 | 168.9 | 50 | 20. | 11.12 | | 88.88 | 1.95 |
| 62 | 169.4 | 50 | 25. | 13.90 | 70 | 86.10 | 1.93 |
| 65 | 168.9 | 50 | 30 | 16.68 | | 83.32 | 1.92 |
| 69 | 171.1 | 50 | 35 | 19.46 | 100 | 80.54 | 1.91 |
| 72 | 170.5 | 50 | 40 | 22.23 | | 77.76 | 1.89 |
| 76 | 172.2 | 50 | 45 | 25.01 | 190 | 74.99 | 1.87 |
| 80 | 172.2 | 50 | 50 | 27.79 | | 72.21 | 1.86 |
| 84 | 173.9 | 50 | 55 | 30.57 | 270 | 69.43 | 1.84 |
| 87 | 173.9 | 50 | 60 | 33.35 | | 66.65 | 1.82 |
| 89 | 173.3 | 50 | 61.8 | 34.35 | 350 | 65.65 | 1.82 |
| 91 | 172.8 | 50 | 63.4 | 35.24 | 410 | 64.76 | 1.81 |
| 93 | 171.7 | 50 | 65.5 | 36.41 | 460 | 63.59 | 1.80 |
| 95 | 171.7 | 50 | 68 | 37.80 | 490 | 62.20 | 1.79 |
| 97 | 171.7 | 50 | 70 | 38.91 | | 61.09 | 1.79 |
| 101 | 176.1 | 50 | 75 | 41.69 | | 58.31 | 1.77 |
| 105 | 176.1 | 50 | 80 | 44.47 | | 55.53 | 1.74 |
| 110 | 178.9 | 50 | 85 | 47.25 | | 52.75 | 1.72 |
| 114 | 178.3 | 50 | 90 | 50.03 | | 49.97 | 1.70 |
| 119 | 182.2 | 50 | 95 | 52.81 | | 47.19 | 1.67 |
| 124 | 182.2 | 50 | 100 | 55.59 | | 44.41 | 1.65 |
| 135 | 185.5 | 50 | 110 | 61.15 | | 38.85 | 1.59 |
| 148 | 190.0 | 50 | 120 | 66.70 | | 33.30 | 1.52 |
| 163 | 195.5 | 50 | 130 | 72.26 | | 27.74 | 1.44 |
| 172 | 199.4 | 50 | 135 | 75.04 | | 24.96 | 1.40 |
| 181 | 201.7 | 50 | 140 | 77.82 | | 22.18 | 1.35 |
| 204 | 208.9 | 50 | 150 | 83.38 | | 16.62 | 1.22 |
| 234 | 216.1 | 50 | 160 | 88.94 | | 11.06 | 1.04 |

EXAMPLE 5

In this example, 348 grams of technical grade pentaerythritol was initially charged into an esterification reactor at the beginning of the reaction together with 355 grams of a $C_5$ acid (valeric acid) and 570 grams of a $C_9$ acid (branched chain iso-$C_9$). Theoretical water was present in an amount of 180 grams. Thereafter, the remaining 500 grams of the $C_5$ acid was added in stages during the esterification reaction. The results are set forth below in Table 4.

TABLE 4

| Time (min) | Temp. (°C.) | Pressure (MM HG) | H2O (ml) | Conv. (%) | Acid (ml) | (100% Conv.) | Log (100% Conv.) |
|---|---|---|---|---|---|---|---|
| 0 | 19.4 | 50 | 0 | 0.00 | | 100 | 2 |
| 12 | 41.7 | 50 | 0 | 0.00 | | 100 | 2 |
| 22 | 79.4 | 50 | 0 | 0.00 | | 100 | 2 |
| 30 | 106.7 | 50 | 0 | 0.00 | | 100 | 2 |
| 42 | 148.9 | 50 | 1 | 0.56 | | 99.44 | 2 |
| 44 | 152.8 | 50 | 1.8 | 1.00 | | 99.00 | 2 |
| 46 | 158.3 | 50 | 2.8 | 1.56 | | 98.44 | 1.99 |
| 48 | 160.5 | 50 | 4.0 | 2.22 | | 97.78 | 1.99 |
| 51 | 162.8 | 50 | 5.2 | 2.89 | | 97.11 | 1.99 |
| 53 | 166.1 | 50 | 9.2 | 5.11 | | 94.89 | 1.98 |
| 54 | 167.2 | 50 | 10 | 5.56 | | 94.44 | 1.97 |
| 56 | 167.8 | 50 | | 0.00 | | 100 | 2 |
| 59 | 169.4 | 50 | 14.7 | 8.17 | | 91.83 | 1.96 |
| 62 | 169.4 | 50 | 19.6 | 10.89 | | 89.10 | 1.95 |
| 66 | 170.0 | 50 | 25.6 | 14.23 | | 85.77 | 1.93 |
| 69 | 169.4 | 50 | 30.0 | 16.68 | | 83.32 | 1.92 |
| 70 | 168.9 | 50 | | 0.00 | | 100 | 2 |
| 73 | 169.4 | 50 | 35.7 | 19.84 | | 80.16 | 1.90 |
| 76 | 168.4 | 50 | 40 | 22.23 | | 77.76 | 1.89 |
| 77 | 168.4 | 50 | | 0.00 | | 100 | 2 |
| 80 | 168.4 | 50 | 45 | 25.01 | | 74.99 | 1.87 |
| 83 | 168.3 | 50 | 50 | 27.79 | | 72.21 | 1.86 |
| 87 | 168.9 | 50 | 54.5 | 30.29 | | 69.70 | 1.84 |
| 90 | 169.4 | 50 | 60 | 33.35 | | 66.65 | 1.82 |
| 98 | 171.1 | 50 | 70 | 38.91 | | 61.09 | 1.79 |
| 107 | 173.3 | 50 | 80 | 44.47 | | 55.53 | 1.74 |
| 116 | 151.7 | 50 | 90 | 50.03 | | 49.97 | 1.70 |
| 126 | 180.0 | 50 | 100 | 55.59 | | 44.41 | 1.65 |
| 138 | 185.0 | 50 | 110 | 61.15 | | 38.95 | 1.59 |
| 151 | 188.3 | 50 | 120 | 66.70 | | 33.29 | 1.52 |
| 166 | 192.8 | 50 | 130 | 72.26 | | 27.74 | 1.44 |
| 176 | 197.8 | 50 | 135 | 75.04 | | 24.96 | 1.40 |

Table 5 below compares the reaction time required in Examples 2–5 to reach a certain percent conversion of technical grade pentaerythritol to its corresponding ester.

TABLE 5

| Conv. of Technical Grade Pentaerythritol | | Time Required to Reach a Certain % Conv. (min) | | | |
|---|---|---|---|---|---|
| ml (H2O) | % Conversion | Ex. 2 | Ex. 3 | Ex. 4 | Ex. 5 |
| 50 | 27.8 | 96 | 80 | 80 | 83 |
| 80 | 44.5 | 118 | 110 | 105 | 107 |
| 90 | 50.0 | 127 | 120 | 114 | 116 |
| 100 | 55.6 | 136 | — | 124 | 126 |
| 160 | 88.9 | 239 | — | 234 | — |

As demonstrated in Examples 2–5 above, the staged addition of the lower boiling point reactant (e.g., acids during the formation of polyol esters) provides an advantage over conventional batch reaction esterification processes (e.g., Ex. 2) in terms of the time required to reach a certain percent conversion to the ester. In Examples 3–5 (staged addition of the lower boiling point reactant) there were significant time savings over Example 2 (conventional batch process) in conversion to equivalent amounts of ester product. Furthermore, the staged addition of the lower boiling point reactant as shown in Example 4, wherein two-thirds of the acid mixture was initially added to the esterification reactor followed by the staged addition of the remaining acid mixture, was somewhat faster than Example 3, wherein only one-half of the acid mixture was initially charged into the reactor.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A process for the esterification of an acid with at least one alcohol which comprises the following steps:

a. adding said acid and at least one alcohol to a reaction vessel to form a reaction mixture, said alcohol having a lower boiling point than said acid and being added in an amount of about 5% to 60% of the stoichiometric requirements of the total alcohol required to react with the said acid;

b. heating said reaction mixture to a temperature at about or above the boiling point of said alcohol and maintaining a pressure sufficient to obtain boiling of said reaction mixture, thereby converting said acid and at least one alcohol to an ester and removing water and a portion of said alcohol from said reaction vessel;

c. monitoring the concentration of said alcohol in step (b); and d. adding additional alcohol to the reaction mixture if said alcohol contained therein as monitored in step (c) falls below a certain predetermined concentration of said alcohol.

2. The process according to claim 1 further comprising the addition of a catalyst to said reaction vessel such that said acid and alcohol are catalytically converted to said ester.

3. The process according to claim 1 wherein said alcohol is present within said reaction mixture in an amount of about 10% to 20% of the stoichiometric requirements of the total alcohol required to react with said acid.

4. The process according to claim 1 wherein said monitoring step is performed by either titrating said reaction mixture to determine its acidity concentration, measuring the water evolved from said reaction mixture, computer modeling of the reaction rate of said reaction mixture, or any other means capable of monitoring the concentration of said alcohol.

5. The process according to claim 1 wherein said acid is either a monobasic or a polybasic acid.

6. The process according to claim 1 wherein said alcohol is at least one alcohol selected from the group consisting of: $C_4$ to $C_{15}$ monohydric alcohols.

7. The process according to claim 1 wherein said ester is selected from the group consisting of: phthalates, adipates and trimellitates.

8. A process for the esterification of at least one acid with a polyhydroxyl compound which comprises the following steps:

a. adding at least one acid and said polyhydroxyl compound to a reaction vessel to form a reaction mixture, said acid having a lower boiling point than said polyhydroxyl compound and being added in an amount of about 5% to 60% of the stoichiometric requirements of the total acid required to react with the said polyhydroxyl compound;

b. heating said reaction mixture to a temperature at about or above the boiling point of said acid and maintaining a pressure sufficient to obtain boiling of said reaction mixture, thereby converting said acid and said polyhydroxyl compound to an ester and removing water and a portion of said acid from said reaction vessel;

c. monitoring the concentration of said acid in step (b); and d. adding additional acid to the reaction mixture if said acid contained therein as monitored in step (c) falls below a certain predetermined concentration of said acid.

9. The process according to claim 8 further comprising the addition of a catalyst to said reaction vessel such that said acid and said polyhydroxy compound are catalytically converted to said ester.

10. The process according to claim 8 wherein said acid is present within said reaction mixture in an amount of about 10% to 20% of the stoichiometric requirements of the total acid required to react with said polyhydroxy compound.

11. The process according to claim 8 wherein said monitoring step is performed by either titrating said reaction mixture to determine its acidity concentration, measuring the water evolved from said reaction mixture, computer modeling of the reaction rate of said reaction mixture, or any other known means capable of monitoring the concentration of said acid.

12. The process according to claim 8 wherein said acid is at least one acid selected from the group consisting of: monobasic acids and polybasic acids.

13. The process according to claim 8 wherein said polyhydroxy compound is an aliphatic polyhydric alcohol comprising about 2 to 10 primary hydroxyl groups.

14. The process according to claim 8 wherein said ester is a polyol ester.

15. A process for the esterification of an anhydride with at least one alcohol which comprises the following steps:

a. adding said anhydride and at least one alcohol to a reaction vessel to form a reaction mixture, said alcohol having a lower boiling point than said anhydride and being added in an amount of about 5% to 60% of the stoichiometric requirements of the total alcohol required to react with the said anhydride;

b. heating said reaction mixture to a temperature at about or above the boiling point of said alcohol and maintaining a pressure sufficient to obtain boiling of said reaction mixture, thereby converting said anhydride and at least one alcohol to an ester and removing water and a portion of said alcohol from said reaction vessel;

c. monitoring the concentration of said alcohol in step (b); and d. adding additional alcohol to the reaction mixture if said alcohol contained therein as monitored in step (c) falls below a certain predetermined concentration of said alcohol.

16. The process according to claim 15 further comprising the addition of a catalyst to said reaction vessel such that said anhydride and at least one alcohol is catalytically converted to said ester.

17. The process according to claim 15 wherein said alcohol is present within said reaction mixture in an amount of about 10% to 20% of the stoichiometric requirements of the total alcohol required to react with said anhydride.

18. The process according to claim 15 wherein said monitoring step is performed by either titrating said reaction mixture to determine its acidity concentration, measuring the water concentration of said reaction mixture, or computer modeling of the reaction rate of said reaction mixture.

19. The process according to claim 15 wherein said anhydride is an anhydride of either a monobasic or a polybasic acid.

20. The process according to claim 15 wherein said alcohol is at least one alcohol selected from the group consisting of: $C_4$ to $C_{15}$ monohydric alcohols.

21. The process according to claim 15 wherein said ester is selected from the group consisting of: phthalates, adipates and trimellitates.

* * * * *